(12) United States Patent
Kim et al.

(10) Patent No.: US 10,406,365 B2
(45) Date of Patent: Sep. 10, 2019

(54) REGENERATIVE INTERFACE ELECTRODE

(71) Applicant: Board of Regents, The University of Texas System, Austin, TX (US)

(72) Inventors: Young-Tae Kim, Arlington, TX (US); Mario Romero-Ortega, Arlington, TX (US); Muthu Wijesundara, Fort Worth, TX (US); Caleb Nothnagle, Fort Worth, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/111,781

(22) PCT Filed: Mar. 14, 2015

(86) PCT No.: PCT/US2015/020631
§ 371 (c)(1),
(2) Date: Jul. 14, 2016

(87) PCT Pub. No.: WO2015/109342
PCT Pub. Date: Jul. 23, 2015

(65) Prior Publication Data
US 2016/0339249 A1    Nov. 24, 2016

Related U.S. Application Data

(60) Provisional application No. 61/927,388, filed on Jan. 14, 2014.

(51) Int. Cl.
*A61N 1/36*    (2006.01)
*A61N 1/05*    (2006.01)

(52) U.S. Cl.
CPC ....... *A61N 1/36103* (2013.01); *A61N 1/0556* (2013.01)

(58) Field of Classification Search
CPC .......................... A61N 1/36103; A61N 1/0556
USPC .......................................................... 607/118
See application file for complete search history.

(56) References Cited

U.S. PATENT DOCUMENTS

| 7,881,036 B2 | 2/2011 | Fujisawa | |
| 2008/0319506 A1* | 12/2008 | Cauller | A61N 1/0536 607/46 |
| 2009/0040681 A1* | 2/2009 | Fujisawa | H01L 21/68 361/234 |

(Continued)

OTHER PUBLICATIONS

International Search Report PCT/US15/20631 dated Jul. 1, 2015.
Written Opinion of the International Searching Authority PCT/US2015/020631 dated Jul. 1, 2015.

*Primary Examiner* — Carl H Layno
*Assistant Examiner* — Erin M Piateski
(74) *Attorney, Agent, or Firm* — FisherBroyles LLP (57) ABSTRACT

A regenerative interface electrode comprising a multilayer or sandwiched stack of dies that are oriented at their distal ends with at least one layer inset such that it forms a groove into which a nerve may be positioned inside the groove. The die layers include electrodes that connect to the nerve, allowing the nerve to be modulated. The electrodes in the die layers are connected to a PCB, which may communicate with a recording device. The distal end of the sandwiched die layers forming the groove is inserted into a nerve tube, into which the nerve is inserted.

20 Claims, 5 Drawing Sheets

(56) References Cited

U.S. PATENT DOCUMENTS

| | | | |
|---|---|---|---|
| 2010/0211172 A1* | 8/2010 | Bellamkonda | A61B 5/0031 623/11.11 |
| 2011/0257501 A1 | 10/2011 | Huys | |
| 2014/0005763 A1 | 1/2014 | Cederna | |

* cited by examiner

REGENERATIVE INTERFACE ELECTRODE

CROSS-REFERENCE TO RELATED APPLICATIONS

This application relates to a U.S. provisional application entitled "Regenerative Interface Electrode," Appl. No. 61/927,388, which was filed on Jan. 15, 2014, and from which this application claims priority. This application is a National Stage application under 35 U.S.C. § 371 of International Application No. PCT/US15/20631, filed on Mar. 14, 2015.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to the field of nerve-electrode interfaces. More particularly, the invention relates to electrodes for use in neuromodulation (recording, stimulating and blocking neural activities) in a patient who has suffered acute nerve damage or amputation.

More than 1.7 million people suffer from limb loss in the United States and this number is estimated to increase by 185,000 a year for upper extremity loss alone (Owings and Kozak 1998). In recent years, much progress has been made to improve the simple robotic prosthetics clinically available, and to create devices with up to 22 degrees of freedom capable of performing complex movements closely resembling those of the lost human arm/hand in amputees (Carpaneto, Micera et al. 2003). Interfacing electrodes in the peripheral nervous system of amputees have allowed users to exert simple control over robotic prosthetics devices (Dhillon and Horch 2005, Di Pino, Guglielmelli et al. 2009). However, providing natural motor control and feel to amputees remains a formidable challenge.

It has been previously demonstrated that peripheral nerves, whether acutely injured or implanted after months of chronic amputation, can be interfaced by enticing them to grow in close proximity to electrodes placed in a tridimensional open regenerative multielectrode interface (REMI) (Garde, Keefer et al. 2009). However, nerves contain a mixture of sensory and motor neurons and neither the REMI nor any of the other currently available types of electrode interfaces can distinguish the specific type of neuron from which they are recording, which limits greatly the effectiveness of the neural interface.

Current regenerative nerve electrodes are limited in interfacing with nerves of a relatively large size, and have poor signal-to-noise ratios that inhibit muscle control and limit accurate sensory information contained within the signals. While some current designs can handle nerves as small as 200 microns in diameter, their configurations only allow for two to three channels within the small physical space. It would be advantageous to design a regenerative multielectrode interface that can accommodate smaller diameter nerves while increasing the number of electrodes or channels. This would increase muscle control by allowing smaller nerves to be controlled with a clearer signal. The improved signal-to-noise ratio would also improve the sensory information obtained.

BRIEF SUMMARY OF THE INVENTION

The present invention solves these limitations by creating a multi-layered sandwich of electrodes with a narrow groove to accommodate smaller nerves, and permit an order of magnitude more channels or electrodes that attach to a particular nerve. The result is a regenerative multielectrode interface (REI) that can house nerves as small as 10 microns in diameter while providing—in the preferred embodiment—32 electrodes or channels on each interface. A plurality of interfaces may be configured either longitudinally along the nerve tube, or axially, or both, to increase the electrodes attached to a particular nerve, thereby creating up to hundreds of channels. This greatly increases the signal-to-noise ratios, allowing for greatly improved sensory information, and greatly increased muscle control.

The RIE is placed between the transected ends of an end-to-end repaired nerve. Generally, the RIE consists of a Bio-synthetic Nerve Implant (BNI) tube, a stacked die set with 32 electrodes, a printed circuit board (PCB) that holds the die set, and a set of connecting cables with end connectors for interfacing with a recording instrument.

The present invention further provides a method of regenerating or growing peripheral nerves in a patient by placing the RIE of the invention between the transected ends of an end-to-end repaired nerve and modulating the nerve.

BRIEF DESCRIPTION OF THE SEVERAL VIEWS OF THE DRAWINGS

The accompanying drawings illustrate the invention, where like reference numerals indicate the same feature throughout the drawings.

DETAILED DESCRIPTION OF THE INVENTION

1. Definitions

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

2. Preferred Embodiment

Selective microelectrodes used in the nervous system are an important and widely used tool to study neural coding in experimental electrophysiology, as well as to diagnose clinical pathologies of the peripheral nervous system. The extracellular recordings made through these electrodes consist of mixed extracellular action potentials (AP). The specific type of nerve fiber close to the electrode cannot be determined with current technology in vivo or from microelectrode arrays.

It has been well established that different neurons have specific conduction velocities. The inventors have designed a new type of REMI with the potential for determining electrode-fiber distance and thus measure conduction velocity. The regenerative interface electrode (RIE) of the invention measures the average time delay between the rostral and caudal electrodes in the cage and, based on a known separation distance between electrodes, determines the conduction velocity.

There are approximately 14000 axons/mm$^2$ in the regenerated sciatic nerve, and about 2.5 nodes/mm axon length, which indicates a probable node density of about 3.5×1 nodes/mm$^3$. For instance, Alpha fibers motor and proprioceptive fibers of the A type have conduction velocities of 70 to 120 meters per second and range from 13 to 22 μm in diameter, whereas B fibers myelinated preganglionic autonomic axons have a fiber diameter of ≤3 μm and a conduction velocity of 3 to 15 meters per second.

The present invention provides means to grow peripheral nerves in an amputee, or to repair damaged peripheral nerves in a patient who has suffered acute nerve injury. The RIE is implanted into the patient at the location of the damaged nerves or amputation, between the transected ends of an end-to-end repaired nerve. The acutely injured or damaged nerves at the location of amputation are enticed to grow in close proximity to the RIE. Due to the configuration of the RIE of the invention, the nerve types are distinguished, resulting in an improved neural interface.

The present invention also enables smaller diameter nerves or nerve bundles to be housed in the RIE than current technology, and provides substantially more electrodes that results in greatly increased signal-to-noise ratios when used. This increases sensory information obtained through the device, and provides greater control of muscle contractions.

Figure 1:
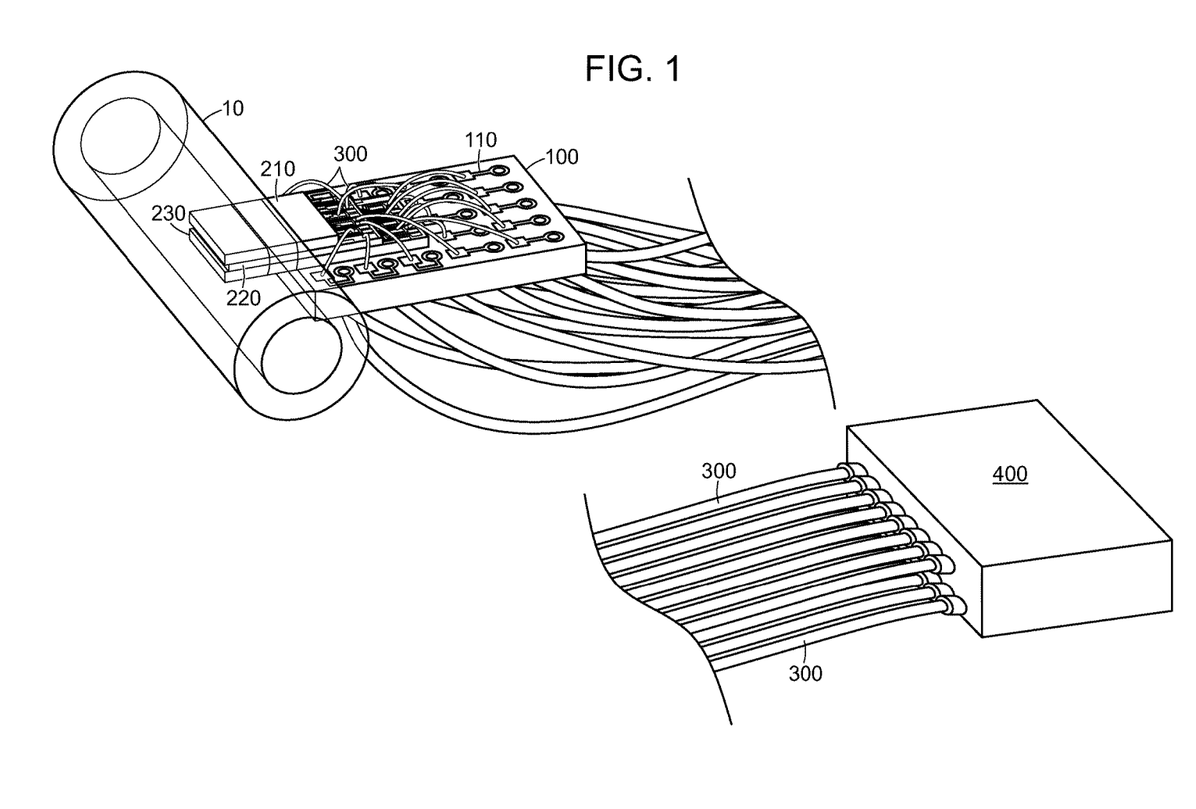
FIG. 1 shows a 3-dimensional depiction, with a cut-away, of the preferred embodiment of the present invention.
Figure 5:
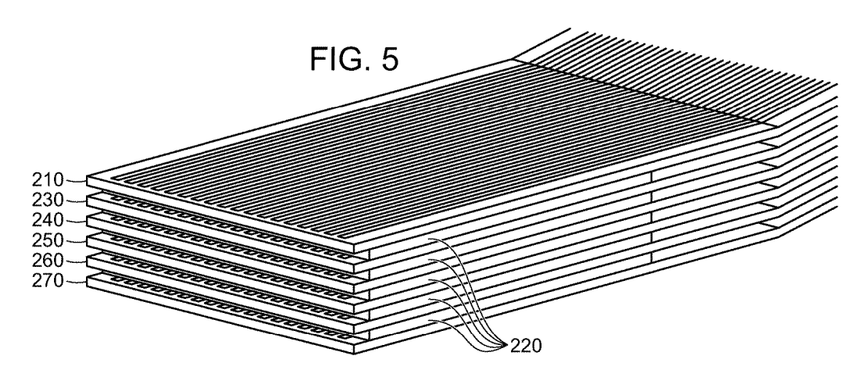
FIG. 5 shows a 3-dimensional depiction of an alternate embodiment of the present invention shown in FIG. 1 in which the microchannel electrode array contains a 13-layer sandwich instead of only three layers, creating six parallel grooves.
Figure 6:
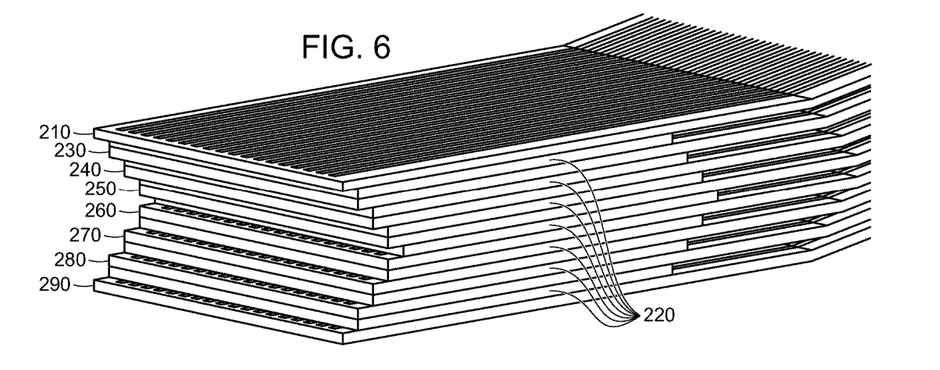
FIG. 6 shows a 3-dimensional depiction of another alternate embodiment of the present invention shown in FIG. 1 in which the microchannel electrode array contains a 15-layer sandwich instead of only three layers, and in which the layers are off-set to create a large groove with a small groove in the center portion.

FIG. 1 shows the preferred embodiment of a single RIE of the present invention. Many embodiments of this RIE possible where multiple units are attached to a single nerve or axon, such as that shown in FIGS. 3-4. Two alternate embodiments of the RIE are shown in FIGS. 5-6.

As shown in FIG. 1, the RIE comprises nerve tube 10, preferably a Bio-synthetic Nerve Implant (BNI) tube, into which a nerve or nerve bundle is inserted. Nerve tube 10 preferably measures approximately 8 to 10 mm in length, has an inner diameter of approximately 1.75 mm, and an outer diameter of approximately 3 mm. T4 silicone is used to protect the wire bonds and adhere the tube and wires to PCB 100. The length of the tube can vary but preferably is from 4-10 mm. Anything shorter would be difficult to suture and anything longer would take too long to grow a nerve through.

The RIE further comprises stacked dies 210, 220 and 230, each layer of which include a set of electrodes, and which is inserted into nerve tube 10. This may be accomplished using tweezers. A window into the side of nerve tub 10 must be cut so as to fit nerve tube 10 over the stacked dies 210, 220 and 230. These cuts may be made by a razor blade, scissors, or laser. One technique entails placing nerve tube 10 over a wide-gauged syringe and cutting the opening using a razor blade, although a laser typically produces better accuracy and fit. Nerve tube 10 is then cut to a length of 8 mm with the window centered in the length of the tube.

Nerve tube 10 is sealed around stacked dies 210, 220 and 230 using T4 Silicone, using a syringe along the edges of the opening while being careful to not push excess silicone into nerve tube 10 where it may block the path of the nerve's growth or cover the electrodes.

Stacked dies 210, 220 and 230 are bonded together using conventional means, and stacked dies 210, 220 and 230 are collectively positioned on one end of printed circuit board (PCB) 100 such that they extend beyond the end of PCB 100, preferably by approximately 1.6 mm. This length can be varied by 1-2 mm, depending upon diameter of the nerve tube 10. PCB 100 preferably has the dimensions of 4 mm by 6 mm with a thickness of 0.7 mm.

Stacked dies 210, 220 and 230 are fabricated on silicon wafers using patterning and metal deposition techniques. Fabrication begins on 200-µm thick, 4-inch, double-sided polished silicon wafers coated with a 500-nm layer of silicon dioxide to create an insulating layer. Either liftoff or etching procedures may be used to achieve the electrode features for the RIE—etching is preferred for thin depositions of metal and liftoff is preferred for thicker layers. Metal deposition may be accomplished by sputtering, evaporation, or electroplating.

One approach used by the inventor is to use a liftoff procedure with a combination of sputtering and evaporation, thereby developing a pattern using conventional lithography techniques. A thick layer of metal is thus deposited and "lifted off" the metal, leaving the metal features adhered to the wafer. This process creates a 3-µm layer of gold features on a single side of a silicon wafer for stacked dies 210 and 230. The process may then be repeated to add a 1.5-µm layer of gold tin to certain areas of these features. For stacked die 220, a separate wafer is used where aligned patterns fabricate only gold features onto the top and bottom of a wafer. The wafers are then singulated using a dicing saw to control the distance of the electrodes from the edge of the dies.

A flip-chip bonder may be used to bond stacked dies 210, 220 and 230 together. A piranha solution and plasma chamber are employed to heavily clean stacked dies 210, 220 and 230, then the gold tin and gold features of the stacked two dies are aligned and bonded using heat and pressure. A 20-minute bond process is then employed where the temperature and pressure is ramped up to 312° C. and 7500N, is held at that temperature and pressure for a brief period of time, then is slowly ramped back down to room temperature and ambient pressure. The process is then repeated to bond the third die to the other two.

Stacked dies 210, 220 and 230 are then placed onto PCB 100 using a flip-chip bonder, a pick and place system, or similar system for accurate placement. A very small application of Loctite 242 is preferably used in gluing the stacked dies 210, 220 and 230 to PCB 100. Glue is applied while these parts are held together for approximately 20 minutes.

Connecting cables 300 connect the electrodes (e.g., electrode 110) on PCB 100 to the corresponding electrodes on stacked dies 210, 220 and 230. Stacked dies 210, 220 and 230 preferably contain 32 electrodes, which extend along the surface of each of stacked dies 210, 220 and 230 to the end of stacked dies 210, 220 and 230 that is inserted into nerve tube 10.

The electrodes on PCB 100 are also connected to recording instrument 400 via connecting cables 300, which are connected to the bottom portion of PCB 100. The composition and relationship of the electrodes (e.g., electrode 110) are well known to those skilled in the art.

The wiring of PCB 100 involves placing PCB 100 into a vice with the wire bonds and stacked dies 210, 220 and 230 facing downwards, with only the backside of PCB 100 exposed. From here, the vias are visible while the delicate wire bonds stay protected on the opposite side. Stripped wires from an Omnetics connector can then be dipped into a conductive silver epoxy and then placed into the vias where, upon drying, a connection will be made through the epoxy. The drying rate of the epoxy can be increased by blowing the wet connection with a heated SMT air soldering gun or similar hot air gun.

T4 Silicone can be used to protect and solidify the wire bonds along with the joints between the Omnetics connector wires and PCB. The silicone is applied onto the wire bonds using a syringe to slowly place a drop onto the surface of the stacked die set's bonding pads and flow/direct more silicone over the wire bonds until a sufficient height and area is reached to cover all of them. A similar process is repeated on the other side of the PCB for the wiring joints. Again, like in the case of the silver epoxy, heat from a SMT solder gun or other heat gun is used to increase the curing rate of the silicone.

For some applications, cable connectors 300 that connect PCB 100 to recording instrument 400 may be eliminated and replaced by wireless connection, which may be any microcontroller module that can measure electrical signals and transmit the information wirelessly. This is particularly advantageous when recording instrument 400 is located outside the patient's body. Alternately, the signals from PCB 100 can be transmitted directly to a prosthetic device within the patient's body, thereby eliminating running wires through the patient's body. Another option is to replace cable connectors 300 with an analog system that transmits signals representing battery life for the battery of the RIE (not shown in the drawings).

Figure 2:
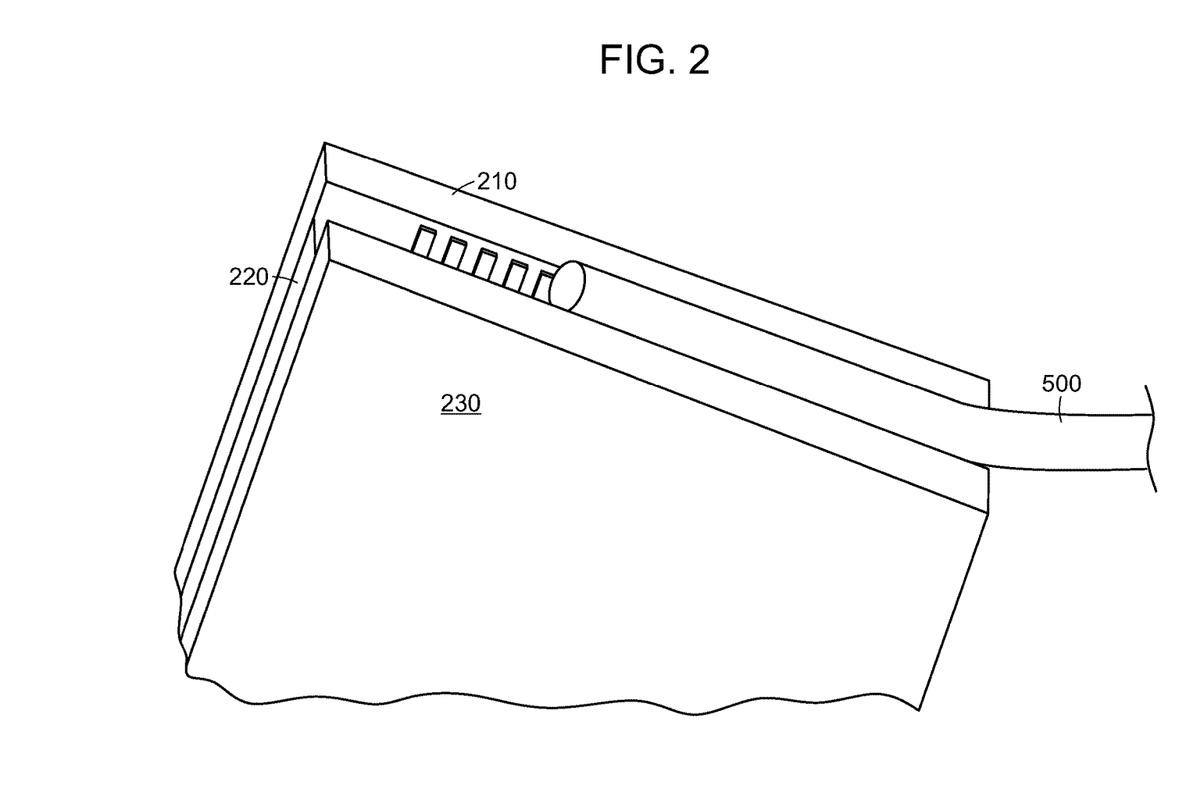
FIG. 2 shows a 3-dimensional depiction of the groove portion of the sandwiched 3-layer configuration of the preferred embodiment of the present invention with a nerve positioned within the groove.

FIG. 2 shows the distal end of stacked dies 210, 220 and 230 that is inserted into nerve tube 10 (for clarity of the drawing, nerve tube 10 is not shown in FIG. 2), where each of stacked dies 210, 220 and 230 is oriented to form a U-shaped groove at their distal ends into which nerve 500 is inserted. In particular, stacked die 220 is inset relative to stacked dies 210 and 230, thereby forming the groove. The thickness of each layer of stacked dies 210, 220 and 230 is such that the groove can accommodate nerve 500 where the diameter of nerve 500 is as small as 10 microns.

Nerve 500 is inserted into and rests within the groove formed by stacked dies 210, 220 and 230 and makes contact with gold-plated electrode pads that are attached to the electrodes on stacked dies 210, 220 and 230. The increased number of electrodes of the present invention compared to that in prior-art devices greatly increases the signal-to-noise ratio, increasing muscle control and sensory information.

The orientation of stacked dies 210, 220 and 230 leave an area of approximately 2000 µm$^2$ of gold trace exposed at the tip of the RIE. The U-shaped groove or channel measures 200 µm wide with walls of 100 µm tall, of which the exposed electrodes have the dimensions of 40 µm wide by 50 µm tall at a pitch of 100 µm, with a 60-µm gap between each electrode. These dimensions are optimized for reading the neural output of a rat; given different requirements, the exposed area, thickness of the silicon dies, and channel depth could all be adjusted to meet any particular application, which will be apparent to those skilled in the art.

Stacked dies 210, 220 and 230 are properly positioned and glued to PCB 100, then cable connectors 300 are electrically connected the gold traces of stacked dies 210, 220 and 230 by wire bonding to the electrical pathways of PCB 100 (e.g., electrode 110). The wire bonds are preferably about 25 µm in diameter, and connect electrode pads on stacked dies 210, 220 and 230 to the gold wire bonding pads on PCB 100, which preferably have a thickness of approximately 100 nm. These wire bonding pads are connected to 0.2 mm gold plated vias which extend through PCB 100 to its backside.

Wires at a length of 5 to 6 cm may be inserted into the vias and lead to an 18-pin Omnetics connector. This length of wire is enough to lead from the nerve inside of a rodent specimen's leg to a spot on top of the rodent's back, outside of the skin. The length of wire may be easily adjusted by the skilled artisan for use in human patients, depending upon the placement of the RIE in the patient. A 36 AWG single core copper wire is preferably used.

Stacked dies 210, 220 and 230 are preferably comprised of a thin layer of silicon dioxide coating. Stacked dies 210 and 230 each contain 15 gold traces on a single side of the die with a thickness of approximately 3 µm. An additional 1.5 µm of gold tin is stacked on top of selected areas of those traces to be used for adhesion during bonding. The thickness of the electrical traces on these devices range from 100 nm to 10 µm or more depending on requirements for bond strength and how they are stacked together. Additionally, the number of traces can be adjusted to the length available on stacked dies 210, 220 and 230 given variable dimensions in their width.

Stacked die 220 preferably has 15 gold traces on each side (front and back) measuring approximately 3 µm in thickness. These electrical traces may be made with various materials ranging from gold, copper, nickel, or even aluminum just so long as resistance is kept below 30 kΩ between the exposed electrodes and the connector. Other materials, such as glass, polyimide, or Kapton, may be used as substrates for these dies. Kapton in particular would allow for a variety of alternative electrode designs, and provide transparency that could greatly aid a surgeon in inserting nerve 500 into the groove formed by stacked dies 210, 220 and 230.

The gold electrode traces may be coated with parylene and then selectively uncoated within a desired area by laser sintering. This allows for a selected area of the gold electrode pads to be exposed without requiring an additional chip or substrate to be placed on top of them. A single strip of cable may thus serve as an electrode without any additional parts outside of nerve tube 10, greatly reducing manufacturing time and cost by eliminating the need for the rest of the packaging (e.g., PCB, die attachment, wire bonds, and wiring).

The bonding pads of stacked dies 210, 220 and 230 are preferably connected to PCB 100 using a 25-µm gold wire. This process involves long wire bonds whose height must be restricted so as to not stick above the top level of stacked dies 210, 220 and 230.

Optionally, a flex cable may be used to replace the substrate of stacked dies 210, 220 and 230, PCB 100, and connecting cables 300 to take advantage of its thin and flexible nature. Flex cables enable the creation of electrode arrays of various shapes and sizes, and allows for a greater number of electrode substrates to be stacked together into the same area, such as the alternate multi-layer embodiments shown in FIGS. 5-6. Kapton cables with electrode traces on either side may be used to both bond the cables together and restrict the exposure of the electrodes.

The Kapton cables may be a polymer substrate with electrical traces made of gold, copper, nickel, or other applicable conductive materials running the length of the cable. These traces act as both the electrodes at the tip and replace all of the wiring leading up to the connector. Flexi-cable can range in thickness between 25 µm and 100 µm, enabling greater variation in the design of electrodes and cabling.

Figure 3:
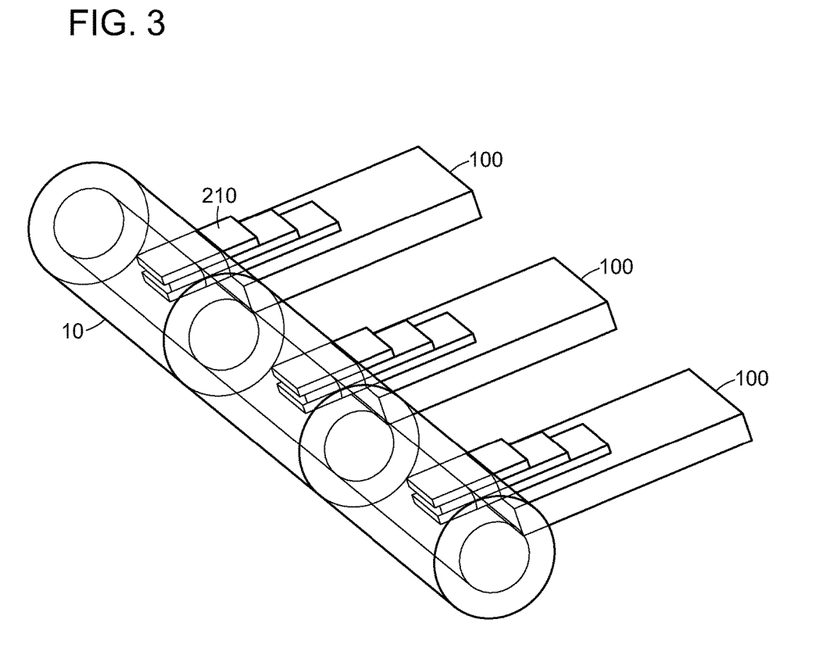
FIG. 3 shows a 3-dimensional depiction of an embodiment of the present invention shown in FIG. 1 in which three microchannel electrode arrays are inserted into a single nerve tube in a linear orientation along the longitudinal axis of the nerve tube.
Figure 4:
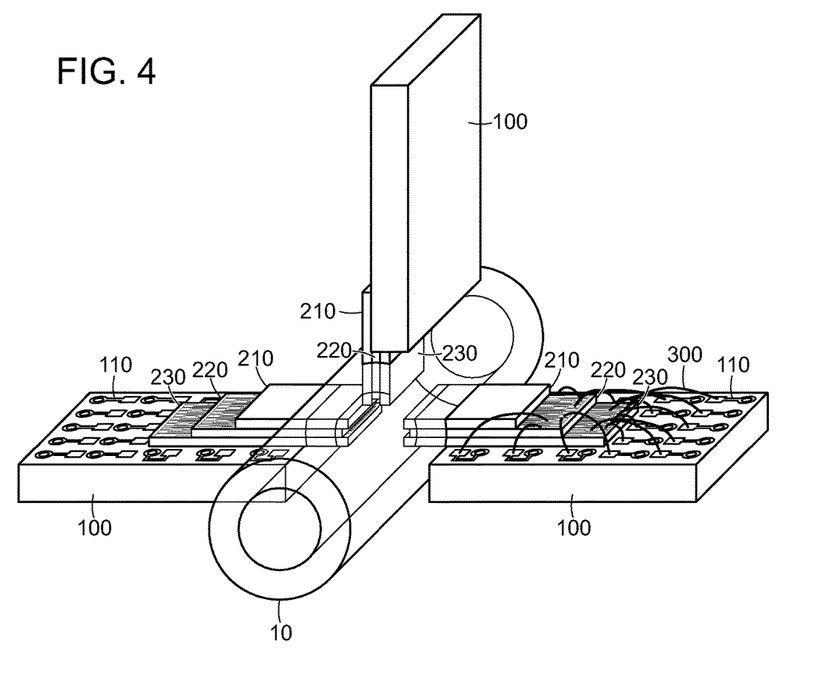
FIG. 4 shows a side view of another embodiment of the present invention shown in FIG. 1 in which three microchannel electrode arrays are inserted into a single nerve tube radially.

FIGS. 3 and 4 show embodiments that configure multiple RIE's of the present invention for use with a single nerve or nerve bundle housed in a single nerve tube 10. In FIG. 3, the RIEs are placed in series linearly along the longitudinal axis of nerve tube 10. The advantage of this configuration is that one can measure the signal delay and activate or control a particular corresponding portion of the nerve, and know how fast to deliver the information or electrical signal. Neuro-modulation can be achieved, thereby allowing the RIEs to record, stimulate the nerve, or block electrical signal from the nerve.

In FIG. 4, the RIEs are positioned circumferentially, or radially, along nerve tube 10. This configuration is useful to attach electrodes to all sides of a nerve bundle. In some application of nerve bundles, combining the configuration shown in both FIGS. 3 and 4 may be desirable.

3. Alternate Embodiments

The preferred embodiment shows a 3-layer stacked die configuration; however, some applications would benefit from various multi-layer stacked die configurations. FIG. 5 shows a 13-layer stacked die configuration with stacked die 210 and 230 sandwiching stacked die 220 as in the preferred embodiment shown in FIG. 1, but having five additional stacked die 220 layers (that is, layers that are inset to form a groove to house a nerve), each separated by stacked die layer 240, 250, 260 and 270.

FIG. 6 shows a V-shaped configuration.

Various other modifications may be made to that depicted in the various drawings of the preferred embodiment of the present invention without departing from the spirit and scope of the invention. Accordingly, the invention is not to be limited by the preferred embodiment shown in the various drawings and described herein, but by the scope of the claims.

Main use is neuro-modulation. Stimulation nerve to make them fire. Not for regeneration. The main diff in 5 and 6 we want to maximize the contact of electrodes to the nerve. More electrode contacts. V-shape configuration.

The invention claimed is:

1. A regenerative interface electrode comprising:
   a first and second die layer each having a distal end adjacent to each other, each of the first and second die layers including a plurality of electrodes; and
   a third die layer positioned between the first and second die layers and having a distal end adjacent to the distal ends of the first and second die layers, and further having a plurality of electrodes;
   wherein the third die layer is further positioned so that it is inset relative to the distal ends of the first and second die layers, thereby forming a groove bounded by the distal ends of the first, second and third die layers; and
   wherein a nerve may be positioned within the groove and make contact with at least some of the electrodes of the first, second and third die layers such that the nerve may be modulated.

2. The regenerative interface electrode of claim 1 where the first, second and third die layers comprise at least 16 electrodes.

3. The regenerative interface electrode of claim 1 where the first, second and third die layers comprise at least 32 electrodes.

4. The regenerative interface electrode of claim 1 further comprising:
   a PCB having a plurality of electrodes; and
   a set of cable connectors that connect each electrode of the printed circuit board to an electrode on one of the first, second and third die layers.

5. The regenerative interface electrode of claim 4 further comprising:
   a recording device; and
   a plurality of connecting cables that attach each of the electrodes on the printed circuit board to the recording device.

6. The regenerative interface electrode of claim 1 in which the first, second and third die layers are made of silicon.

7. The regenerative interface electrode of claim 6 where the first, second and third die layers comprise at least 32 electrodes.

8. The regenerative interface electrode of claim 1 in which the first, second and third die layers comprise polyimide.

9. The regenerative interface electrode of claim 8 where the first, second and third die layers comprise at least 32 electrodes.

10. The regenerative interface electrode of claim 1 further comprising a nerve tube into which the distal ends of the first, second and third die layers are inserted.

11. A process for modulating a nerve comprising the steps of:
constructing a multilayer die having a first, second and third die layer in which the third die layer is positioned between the first and second layer, where each of the first, second and third die layer have a distal end that is proximate to each other, and in which the distal end of the third die layer is inset relative to the position of the distal ends of the first and second die layers, thereby forming a groove, wherein each of the first, second and third die layers have a plurality of electrodes that extend into their distal ends;
inserting a nerve into the groove such that the nerve makes contact with the plurality of electrodes; and
modulating the nerve.

12. The process for modulating a nerve of claim 11 in which the first, second and third die layers are made of silicon.

13. The process for modulating a nerve of claim 11 in which the first, second and third die layers comprise polyimide.

14. The process for modulating a nerve of claim 11 in which the distal ends of the first, second and third die layers are inserted into a nerve tube, and in which the nerve is inserted into the nerve tube prior to being positioned in the groove.

15. The process for modulating a nerve of claim 14 in which the first, second and third die layers are attached to a printed circuit board having a plurality of electrodes by a plurality of connecting cables, each connecting cable attached to an electrode on the printed circuit board that corresponds to an electrode on one of the first, second and third die layers.

16. The process for modulating a nerve of claim 11 in which the first, second and third die layers comprise at least 16 electrodes.

17. The process for modulating a nerve of claim 11 in which the first, second and third die layers comprise at least 32 electrodes.

18. A regenerative interface electrode system comprising:
a plurality of regenerative interface electrodes, each regenerative interface electrode comprising:
a first and second die layer each having a distal end adjacent to each other, each of the first and second die layers including a plurality of electrodes; and
a third die layer positioned between the first and second die layers and having a distal end adjacent to the distal ends of the first and second die layers, and further having a plurality of electrodes;
wherein the third die layer is further positioned so that it is inset relative to the distal ends of the first and second die layers, thereby forming a groove bounded by the distal ends of the first, second and third die layers; and
a nerve tube;
wherein the distal ends of each of the plurality of regenerative interface electrodes are inserted into the nerve tube;
such that a nerve may be inserted into the nerve tube and positioned within the groove of each of the plurality of regenerative interface electrodes, and such that the nerve may be modulated by the electrodes of the plurality of regenerative interface electrodes.

19. The regenerative interface electrode system of claim 18 in which the plurality of regenerative interface electrodes are inserted into the nerve tube linearly relative to each other along the longitudinal axis of the nerve tube.

20. The regenerative interface electrode system of claim 18 in which the plurality of regenerative interface electrodes are inserted into the nerve tube axially relative to each other such that the electrodes in each regenerative interface electrode can come in contact with a different portion of the nerve circumferentially.

* * * * *